United States Patent
Takahashi

(10) Patent No.: US 8,096,952 B2
(45) Date of Patent: Jan. 17, 2012

(54) ELECTRIC-POWERED AIR RELEASE VALVE AND BLOOD PRESSURE GAUGE

(75) Inventor: Yukio Takahashi, Shibukawa (JP)

(73) Assignee: Japan Precision Instruments, Inc., Gunma (JP)

(*) Notice: Subject to any disclaimer, the term of this patent is extended or adjusted under 35 U.S.C. 154(b) by 1254 days.

(21) Appl. No.: 11/783,612

(22) Filed: Apr. 10, 2007

(65) Prior Publication Data
US 2007/0239042 A1    Oct. 11, 2007

(30) Foreign Application Priority Data
Apr. 11, 2006    (JP) .............................. 2006-109150

(51) Int. Cl.
*A61B 5/02*    (2006.01)
(52) U.S. Cl. ....................... 600/498; 600/485
(58) Field of Classification Search .......... 600/485, 600/490, 492, 495, 498, 500, 502, 504; 251/129.16, 251/129.2, 129.21
See application file for complete search history.

(56) References Cited

U.S. PATENT DOCUMENTS

| | | | |
|---|---|---|---|
| 2,947,284 A | | 8/1960 | Nicholson |
| 4,527,590 A | * | 7/1985 | Kolze ....................... 137/596.17 |
| 4,889,314 A | * | 12/1989 | Hashizume et al. ...... 251/129.02 |
| 5,040,567 A | * | 8/1991 | Nestler et al. ............. 137/625.44 |
| 5,110,087 A | * | 5/1992 | Studtmann et al. ....... 251/129.16 |
| 5,158,263 A | * | 10/1992 | Shimizu et al. ........... 251/129.21 |
| 5,542,428 A | * | 8/1996 | Jayne ............................ 600/494 |
| 5,653,422 A | | 8/1997 | Pieloth |
| 6,311,951 B1 | | 11/2001 | Samulowitz |

FOREIGN PATENT DOCUMENTS

| EP | 0695406 B | 10/1997 |
|---|---|---|
| JP | 06047008 A | 2/1994 |
| JP | 2005155898 A | 6/2005 |

OTHER PUBLICATIONS

Extended European Search Report, which issued on Oct. 30, 2009 in European Patent Application 07105884.6-2422/1847743.

* cited by examiner

*Primary Examiner* — Charles A Marmor, II
*Assistant Examiner* — Tho Tran
(74) *Attorney, Agent, or Firm* — Merek, Blackmon & Voorhees, LLC

(57) ABSTRACT

The electric-powered air release valve comprises a nozzle, a fixed iron core; an excitation coil; a movable iron plate; a leaf spring: a rubber valve; and a yoke; wherein a circular hole capable of accommodating a circular column part at one end of the fixed iron core when the movable iron plate is moved toward the nozzle is formed in the movable iron plate; and a magnetic gap is maintained between an internal periphery of the circular hole and an external periphery of the circular column part at one end of the fixed iron core.

24 Claims, 7 Drawing Sheets

ELECTRIC-POWERED AIR RELEASE VALVE AND BLOOD PRESSURE GAUGE

BACKGROUND OF THE INVENTION

1. Field of the Invention

The present invention relates to an electric-powered air release valve that is particularly suitable for use in an exhaust device for a blood pressure gauge, and to a blood pressure gauge that comprises the electric-powered air release valve.

2. Description of the Related Art

A blood pressure gauge measures blood pressure during the process of gradually reducing the pressure inside a cuff belt after the pressure is increased to a prescribed value. In such a blood pressure gauge, an electric-powered air release valve is used to gradually reduce the pressure inside the cuff belt.

The electric-powered air release valve described in Japanese Patent No. 3029073 is known as a conventional example of an electric-powered air release valve used in a blood pressure gauge. This electric-powered air release valve has a movable coil, and is configured as shown in FIG. 7.

In FIG. 7, the reference numeral 201 indicates the main housing, and 202 indicates the front housing. An airflow channel 203 that passes through a pump, a cuff belt, or the like is provided to the front housing 202 that blocks an opening at the front end of the main housing 201, and one end of the airflow channel 203 leads into the main housing 201 and forms an opening as an air outflow vent (air release vent) 204.

An armature 220 as a movable element is provided in the center inside the main housing 201, and a permanent magnet 210, and yokes 211, 212 are provided on the external periphery of the armature 220. A drive coil 225 installed on the armature 220 is inserted between the yokes 211, 212, and the coil 225 is shaped so as to intersect the magnetic field between the yokes 211, 212.

The head of the armature 220 faces the center of the front housing 202, and a rubber valve (orifice gasket) 230 for opening and closing the air outflow vent 204 is provided to the head so as to face the air outflow vent 204. The armature 220 is also supported in the main housing 201 by two leaf springs 241, 242 at both ends in the movement direction, and is urged by the leaf springs 241, 242 in the valve-opening direction, i.e., the direction in which the rubber valve 230 is separated from the air outflow vent 204.

When blood pressure is measured using this electric-powered air release valve, an electric current that intersects the magnetic field between the yokes 211, 212 is first fed to the coil 225 by supplying electrical power to the drive coil 225. A drive force is then generated in the coil 225, the armature 220 moves against the urging force of the leaf springs 241, 242, and the rubber valve 230 closes the air outflow vent 204. In this state, air is fed into the cuff belt by a pressurizing pump, and the cuff belt is pressurized.

The process of reducing the pressure in the cuff belt then begins. At this time, the drive force generated in the drive coil 225 is continuously weakened by gradually reducing the current fed to the coil 225. The armature 220 is then moved toward the initial position by the urging force of the leaf springs 241, 242, the rubber valve 230 separates from the air outflow vent 204 to gradually open the valve, and the air inside the cuff belt flows through the air outflow vent 204 and escapes to the outside in small incremental amounts. Blood pressure is measured in the process of reducing the pressure inside the cuff belt by the incremental release of small amounts of air.

Besides the technique described in Japanese Patent No. 3029073, Japanese Laid-open Patent Application No. 2005-155898 describes a technique for enabling finer control of the flow rate through a rubber valve by providing small irregularities to the surface of the rubber valve, and managing a minute gap created by the irregularities according to the condition in which the rubber is collapsed when the rubber is pressed against a nozzle (airflow vent).

SUMMARY OF THE INVENTION

Since the conventional electric-powered air release valve operates according to a scheme in which the armature equipped with a coil is moved using the magnetic force of a permanent magnet, a large number of parts are used, the structure is complex, and the moving parts can easily become heavy. There is also a tendency for the weight of the coil to be increased in order to obtain the drive force necessary for complete closure in order to prevent air leakage at the maximum pressure (usually about 280 mmHg to 300 mmHg), and the moving parts can also become heavy.

In order to increase the precision of air release, such moving parts that are apt to be heavy must be smoothly and precisely moved while being urged by springs.

Accordingly, not only is a compact design difficult to achieve, but a painstaking assembly process is needed, and production cost is increased.

Due to the increase in the weight of the moving parts, when the electric-powered air release valve is applied to a wrist-type blood-pressure gauge, for example, the air release characteristics vary according to differences in posture during blood pressure measurement, and the accuracy of measurement can be adversely affected as a result.

In the conventional movable-coil-type electric-powered air release valve in which drive power is created by the intersection of current flowing through a coil in a magnetic field created by a permanent magnet, a force proportional to the current flowing through the coil is generated to adjust the opening of the valve. Therefore, it may appear possible to control pressure reduction in proportion to the current, but when, for example, an irregular surface (in which irregularities are provided to the pressing surface of a rubber valve) of a rubber valve provided for slow air release is pressed, valve characteristics actually occur in which a weak pressing force can be exerted at first, but a strong pressing force must subsequently be exerted each time the amount of opening is increased. As a result, it is difficult to perform control that is proportional to the current fed to the coil, and complex control is impossible to avoid.

The present invention was developed in view of the foregoing drawbacks, and an object of the present invention is to provide an electric-powered air release valve having a simple, compact structure, easy assembly and reduced manufacturing cost, and the capability of demonstrating stable characteristics despite differences in posture, and to provide a blood pressure gauge that is provided with the electric-powered air release valve.

The electric-powered air release valve according to a first aspect of the present invention comprises a nozzle provided as an air discharge vent to an end part of an air channel; a rod-shaped fixed iron core disposed so that an end part in a longitudinal direction is aligned with the nozzle on the same side as the nozzle; an excitation coil provided so as to surround the fixed iron core, for magnetizing the fixed iron core in a longitudinal direction when electrical power is applied; a movable iron plate that is disposed so as to face the nozzle and an end part of the fixed iron core and that moves toward the nozzle from an initial position according to a magnetic attraction force when the fixed iron core is magnetized; a spring for urging the movable iron plate into the initial position; a valve body provided to the movable iron plate, for adjusting an opening amount of the nozzle in accordance with a movement position when the movable iron plate moves toward the nozzle in opposition to an urging force of the spring; and a yoke that is magnetically connected to another end part of the fixed iron core, and whose distal end part is disposed opposite a position separated from an end part of the fixed iron core above the movable iron plate, via a magnetic gap; wherein an opening is formed in the movable iron plate that is capable of accommodating an end part of the fixed iron core when the movable iron plate is moved toward the nozzle, and a magnetic gap is maintained between an internal periphery of the opening and an external periphery of an end part of the fixed iron core.

The invention according to a second aspect is the electric-powered air release valve of the first aspect, wherein the movable iron plate is composed of a panel having a thickness equal to or greater than a maximum amount of movement of the movable iron plate.

The invention according to a third aspect is the electric-powered air release valve of the first or second aspect, wherein a circular hole is formed as the opening in a center part of a width direction of the movable iron plate, and a circular column that can be accommodated by the circular hole is formed at an end part of the fixed iron core.

The invention according to a fourth aspect is the electric-powered air release valve of any of the first through third aspects, wherein a distal end part of the yoke is disposed so as to face side parts of the movable iron plate via the magnetic gap; and a curved machined part for increasing an opposing surface area is provided to at least one area selected from the distal end of the yoke and side parts of the movable iron plate, disposed so as to face each other.

The invention according to a fifth aspect is the electric-powered air release valve of any of the first through fourth aspects, wherein a magnetic channel through the movable iron plate and the magnetic gap of the yoke, and a magnetic channel through the movable iron plate and the magnetic gap of the fixed iron core are disposed in substantially the same plane.

The invention according to a sixth aspect is the electric-powered air release valve of any of the first through fifth aspects, wherein the fixed iron core and the air channel are each provided to an internal side or interior of a bobbin onto which the excitation coil is wound.

The invention according to a seventh aspect is the electric-powered air release valve of the sixth aspect, wherein the bobbin is composed of a resin molding having the air channel and a fitting hole for the fixed iron core; the fixed iron core is fitted into the fitting hole so that one end part of the fixed iron core protrudes from an end of the fitting hole: a nozzle of one end part of the air channel is provided in a position adjacent to one end part of the fixed iron core so as to protrude from one end surface of the bobbin; and another end part of the air channel is provided as an inflow vent to another end surface of the bobbin.

The invention according to an eighth aspect is the electric-powered air release valve of the sixth or seventh aspect, wherein the movable iron plate is cantilevered by the bobbin via a leaf spring as the spring, and the nozzle and valve body are disposed between the movable iron plate and a magnetic attraction point of the fixed iron core at a point at which the movable iron plate is supported.

The invention according to a ninth aspect is the electric-powered air release valve of any of the first through eighth aspects, wherein a distal end of the nozzle protrudes in a chevron shape, a peripheral edge of a distal-end opening of the nozzle is rounded, and a surface of the valve body that presses against the nozzle is formed as a smooth flat surface.

The invention according to a tenth aspect is the electric-powered air release valve of any of the first through ninth aspects, wherein a rubber valve for pressing against a distal end of the nozzle is provided as the valve body.

In the blood pressure gauge according to an eleventh aspect of the present invention, the electric-powered air release valve according to any of the first through tenth aspects is used as an air release valve for discharging air that is fed into a cuff belt wrapped around an arm, wrist, or other part of a body.

According to the first aspect of the present invention, the fixed iron core is magnetized by electric power flowing through the excitation coil, and the movable iron plate is attracted by the magnetic force, whereby the opening of the nozzle is adjusted by the valve body provided to the movable iron plate. A small-sized, compact, and low-cost structure that is simple and has a small number of parts can therefore be created without the use of a permanent magnet having a high unit cost.

A system is adopted in which a movable iron plate equipped with a valve body is attracted by magnetic force, rather than a structure for moving an armature provided with a coil. Therefore, the weight of the moving parts can be reduced, and a simpler assembly process that includes attachment of springs can thereby be anticipated.

Since it is possible to reduce the weight of the moving parts that play an important role in adjusting the opening of the nozzle, it is possible to minimize variations in the valve characteristics caused by the weight of the device acting in different directions according to differences in posture. For example, in applications such as wrist-type blood-pressure gauges that are highly likely to be used in a variety of postures, stable characteristics can be demonstrated, and highly precise measurement can be performed.

In the present invention, a magnetic circuit is formed by the fixed iron core, the yoke, and the movable iron plate that are each provided via a magnetic gap. Leakage of magnetic fluxes is therefore reduced, and current control can be performed with high efficiency and minimal drive loss.

In general, as the current flowing through the excitation coil is increased, the movable iron plate continues to be attracted to the fixed iron core according to the generated electromagnetic force. The attractive force then increases in inverse proportion to the square of the distance between the movable iron plate and the fixed iron core. In this regard, the present invention is configured so that an opening is formed in the movable iron plate, one end part of the fixed iron core penetrates into the opening according to the movement of the movable iron plate, and a magnetic gap is maintained between the internal periphery of the opening and the external periphery of the end part of the fixed iron core, Accordingly, even when the movable iron plate moves according to the magnetic force, the size of the magnetic gap between the movable iron plate and the fixed iron core can be kept substantially constant.

The force of magnetic attraction increases in inverse proportion to the square of the distance (size of the magnetic gap), as previously mentioned. However, since the magnetic gap can be kept substantially constant in the present invention, the relationship between the current fed to the excitation coil and the amount of movement of the movable iron plate can be made approximately linear, and there is no abrupt attraction of the movable iron plate to the fixed iron core as the amount of movement is increased (as the distance decreases in size). In other words, the size of the gap between the nozzle and the valve body can be controlled in approximate proportion to the amount of supplied current, and this gap control enables the amount of released air to be controlled with high precision.

As a result, when the present invention is applied as the air release valve of a blood pressure gauge, the control characteristics at extremely low pressure reduction rates can be improved, and blood pressure can be measured with high precision and with stable pressure reduction characteristics.

In a structure in which the movable iron plate is merely attached by suction parallel to the attachment surface of the fixed iron core, the force of the attachment increases in inverse proportion to the square of the distance. Therefore, when an attempt is made to control the gap relative to the nozzle by using the valve body to which the movable iron plate is attached, the gap becomes difficult to control as the gap is reduced. Accordingly, it is difficult to increase the precision with which minute amounts of airflow are controlled through management of the gap.

Therefore, to address this problem, the valve body is formed using a flexible rubber valve, irregularities are provided to the surface of the rubber valve that presses against the nozzle, the minute gap is substantially managed by the degree to which the irregularities of the rubber valve are collapsed when the rubber valve is pressed against the nozzle, and the amount of air released from the gap (amount of leakage) is adjusted. However, since the collapsibility characteristics the rubber valve are dependent on the hardness of the rubber, and the hardness of the rubber can vary significantly between product lots, the degree to which the rubber valve can be collapsed is difficult to manage on the basis of a constant assumed rubber hardness. Designed air release characteristics are therefore difficult to obtain when this approach is taken in a mass production system.

In this regard, the present invention does not employ a system that depends on the degree to which the rubber valve can be collapsed to perform subtle adjustments of the flow rate, but instead controls the air release flow rate by carefully managing the space (gap) between the valve body and the nozzle with high precision, as previously described. Accordingly, there is no need for dependence on the hardness of the rubber, and the rubber is therefore easy to select. Since there is also no need to manage the essential minute gap in accordance with the degree to which the surface irregularities of the rubber valve can be collapsed, the surface of the rubber valve may simply be a flat surface that has a level of smoothness that prevents adhesion to the nozzle. As a result, the air releasing characteristics of each product in the mass production system are easier to manage, and design/manufacture is facilitated.

According to the second aspect of the present invention, the movable iron plate is composed of a sheet material whose thickness is equal to or greater than the maximum amount of movement of the movable iron plate. Therefore, the opposing surface area of the movable iron plate and the fixed iron core merely varies to a certain degree with changes in the degree to which the fixed iron core penetrates into the opening within the range of the thickness of the movable iron plate, and almost no change is produced in the size of the magnetic gap. Accordingly, the linearity of control can easily be maintained merely by considering the thickness of the sheet material when selecting the material for forming the movable iron plate. Since the movable iron plate is also formed from a sheet material, the opening can easily by formed by punching.

According to the third aspect of the present invention, a circular hole is formed as the opening in the center part in the width direction of the movable iron plate, and a circular column that can be accommodated by the circular hole is formed at one end part of the fixed iron core. A relationship can therefore be established in which the peripheral surfaces face each other via the magnetic gap. Accordingly, effects are obtained whereby bias in the distribution of magnetic fluxes can be minimized, and stable attraction effects can be exerted. Since the circular hole of the movable iron plate, as well as the circular column of the fixed iron core, have shapes that are relatively easy to machine compared to other shapes, dimensional precision is easily obtained, and the distance between the movable iron plate and the opposing part of the fixed iron core, i.e., the magnetic gap, can be reduced, As a result, narrowing the magnetic gap also has the effect of making it easier to increase the drive force.

The relationship between the circular hole and the circular column is also advantageous for assembly. For example, during assembly, a tubular positioning tool is inserted in the gap between the circular column of the fixed iron core and the circular hole of the movable iron plate, and the fixed iron core and movable iron plate are assembled thereon. Both components can thereby be easily positioned, and the precision of assembly can also be increased.

According to the fourth aspect of the present invention, the distal end parts of the yoke are disposed so as to face the side parts of the movable iron plate via the magnetic gap, and curved machined parts for increasing the opposing surface area are provided to the side parts of the movable iron plate that face the end surfaces of the distal end parts of the yoke. The surface area of the magnetic bond can thereby be increased, and the efficiency of the magnetic circuit can be improved.

According to the fifth aspect of the present invention, a magnetic channel between the movable iron plate and the yoke, and a magnetic channel between the movable iron plate and the fixed iron core are disposed in substantially the same plane. Therefore, the path of magnetism from the yoke to the fixed iron core through the movable iron plate can be in a straight line of minimum length, magnetic circuit loss can be reduced, and enhanced drive efficiency can be anticipated.

According to the sixth aspect of the present invention, the fixed iron core and the air channel are each provided to an internal side or interior of a bobbin onto which the excitation coil is wound. Therefore, the nozzle and the valve body can be disposed in a position that is near the point of magnetic attraction between the movable iron plate and the fixed iron core, and the structure that also includes the support part of the movable iron plate can be reduced in size and made simple and compact.

According to the seventh aspect of the present invention, the fitting hole and air channel of the fixed iron core are formed inside a bobbin made of resin, and the nozzle is formed in an end surface of the bobbin. The structure can therefore be simplified, and easy assembly and enhanced production properties can be anticipated.

According to the eighth aspect of the present invention, the movable iron plate is cantilevered by the bobbin via a leaf spring, and the nozzle and valve body (action point) are disposed between the movable iron plate and a magnetic attraction point (power point) of the fixed iron core at a point (support point) at which the movable iron plate is supported. Therefore, the magnetic attraction force acting between the movable iron plate and the fixed iron core can be effectively transmitted as the force for adjusting the gap between the nozzle and the valve body. In other words, the valve body can be moved by a small drive force, and enhanced drive efficiency is anticipated. The placement of the action point (valve body) between the support point (cantilever point) and the power point (magnetic attraction point) helps to reduce the size of the area around the moving part.

It is also possible to place the nozzle and the valve body outside the excitation coil wound onto the bobbin. In this case, however, the distance between the support point and the power point, and the distance between the action point and the power point must be increased, which inhibits size reduction. In this regard, a placement such as the one used in the present invention contributes to reduced size. Since the movable iron plate may also be supported via a cantilevered leaf spring, the movable iron plate can be installed by a simple process. A leaf spring is also used as the spring for urging the movable iron plate. Therefore, the movable iron plate can easily be supported while receiving the urging force, and this arrangement is also effective for making the structure more compact.

According to the ninth aspect of the present invention, the distal end of the nozzle is made to protrude in a chevron shape, the peripheral edge of the distal-end opening of the nozzle is rounded, and the surface of the valve body that presses against the nozzle is formed as a smooth flat surface. The nozzle and the valve body can therefore be brought into contact with each other in a form that approximates line contact rather than plane contact. The gap between the nozzle and the valve body thus becomes easier to manage, and the air release flow rate can be made easier to control. Since the surface of the valve body that presses against the nozzle can be made smooth and flat, machining is facilitated and production capability can be enhanced.

According to the tenth aspect of the present invention, since a rubber valve is used as the valve body, the completely closed nozzle can be made more airtight. As previously described, flow rate adjustment is performed by carefully managing the gap between the rubber valve and the nozzle, and not according to the degree in which the rubber is collapsed. Therefore, the hardness of the rubber valve can be freely selected, and design/manufacturing is facilitated.

According to the eleventh aspect of the present invention, using the electric-powered air release valve according to any of the first through tenth aspects makes it possible to provide a compact, low-cost blood pressure gauge that has stable performance.

BRIEF DESCRIPTION OF THE DRAWINGS

FIG. 1 is a diagram showing the structure of the electric-powered air release valve 10 according to an embodiment of the present invention; wherein FIG. 1A is a plan view; and FIG. 1B is a sectional view along arrow Ib-Ib in FIG. 1A;

FIG. 2 is a schematic view showing sectional views along arrow II-II in FIG. 1A; wherein

FIG. 3 is a schematic enlarged view of the state shown in FIG. 2A; wherein

FIG. 4 is a schematic enlarged view of the state shown in FIG. 2B; wherein

FIG. 5 is a schematic enlarged view of the state shown in FIG. 2C: wherein

DESCRIPTION OF THE PREFERRED EMBODIMENTS

Embodiments of the present invention will be described hereinafter based on the accompanying drawings.

Figure 1:
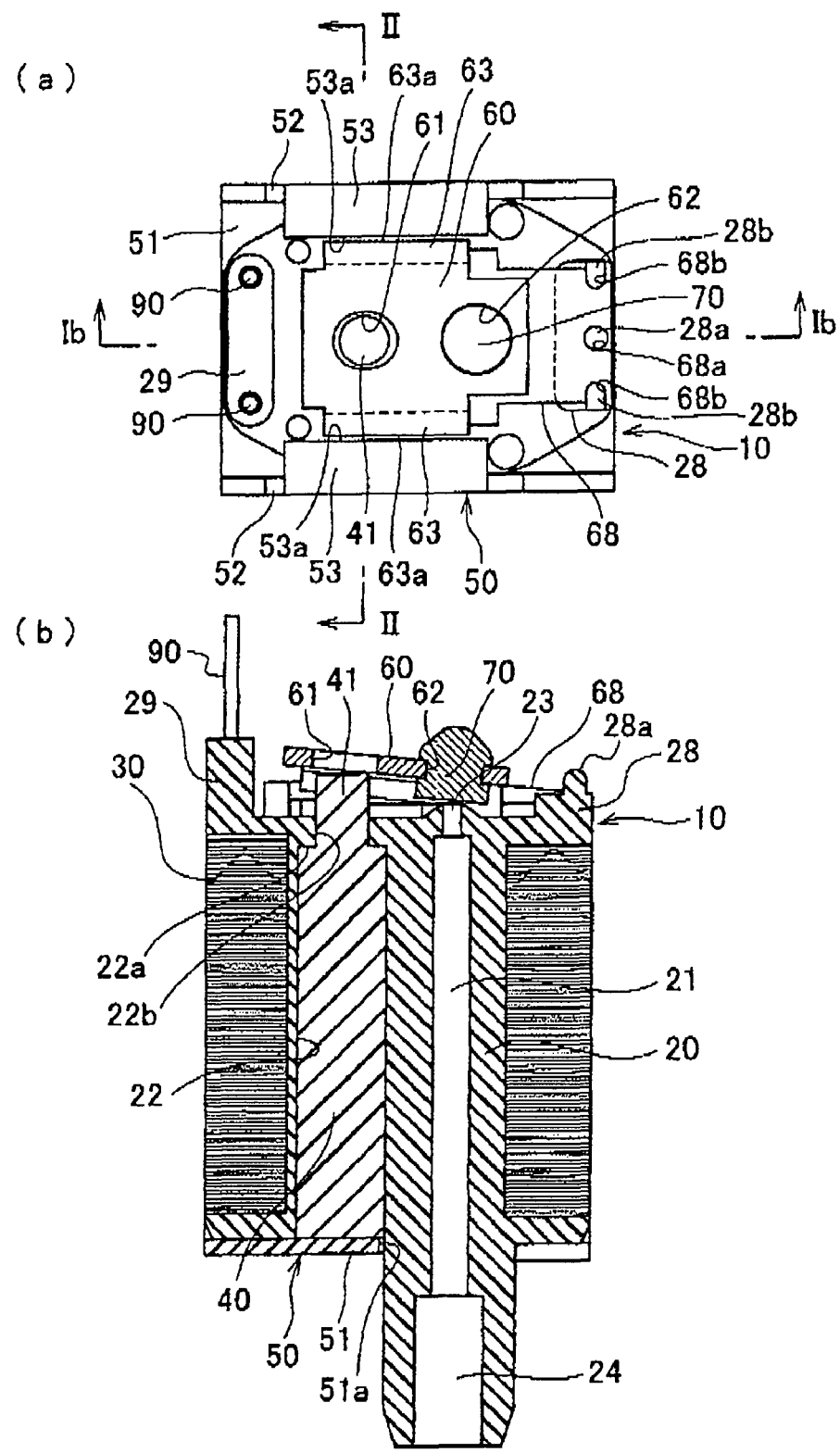
Figure 2A:
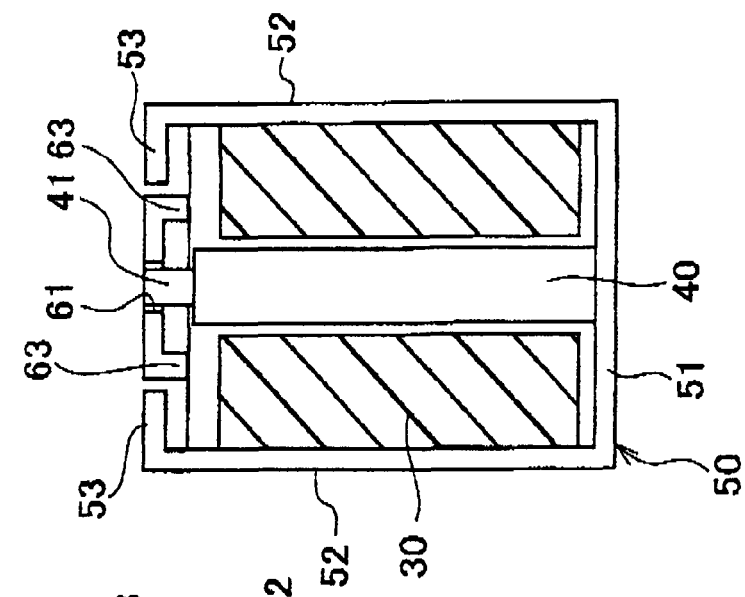
FIG. 2A is a diagram showing an initial state prior to application of drive force, or when drive force begins to be applied.
Figure 2B:
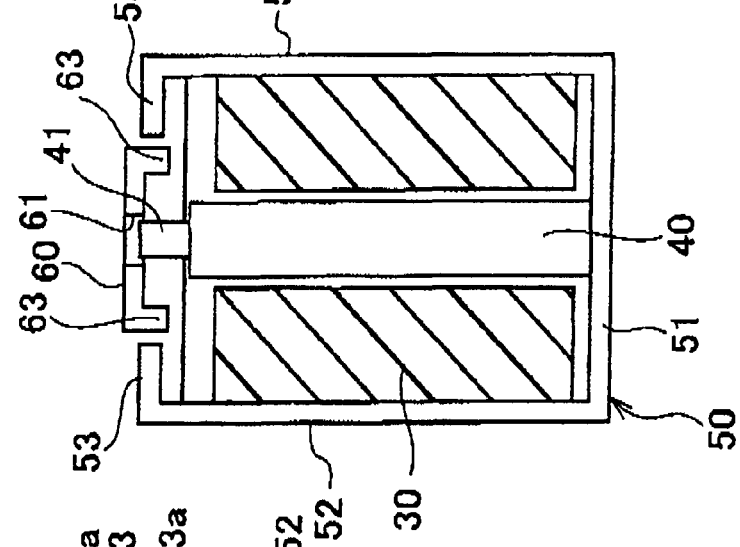
FIG. 2B is a diagram showing a state in which an intermediate drive force is applied.

FIG. 1 is a diagram showing the structure of the electric-powered air release valve 10 according to an embodiment: wherein FIG. 1A is a plan view; and FIG. 1B is a sectional view along arrow Ib-Ib in FIG. 1A. FIG. 2 is a schematic view showing sectional views along arrow II-II in FIG. 1A: wherein FIG. 2A is a diagram showing an initial state prior to application of drive force, or when drive force begins to be applied; FIG. 2B is a diagram showing a state in which an intermediate drive force is applied; and FIG. 2C is a diagram showing a state in which maximum drive force is applied.

Figure 2C:
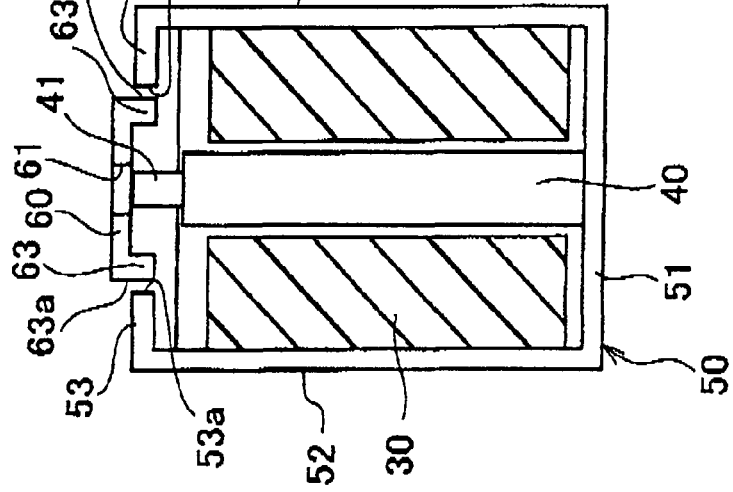
FIG. 2C is a diagram showing a state in which maximum drive force is applied.
Figure 3A:
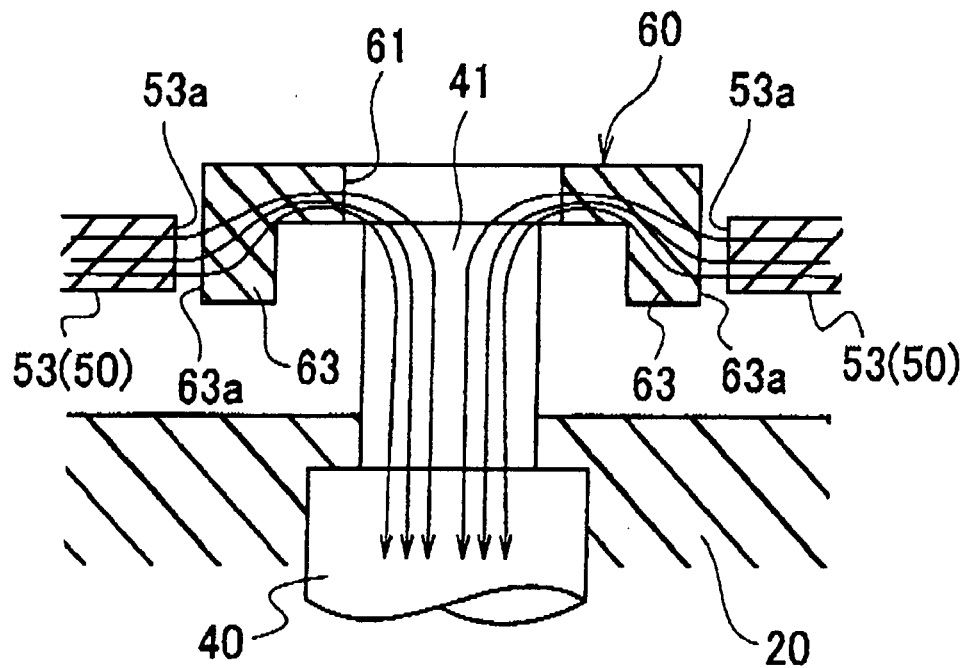
FIG. 3A is a diagram showing a simple enlargement of the relevant parts of FIG. 2A along with the path of magnetic fluxes.
Figure 3B:
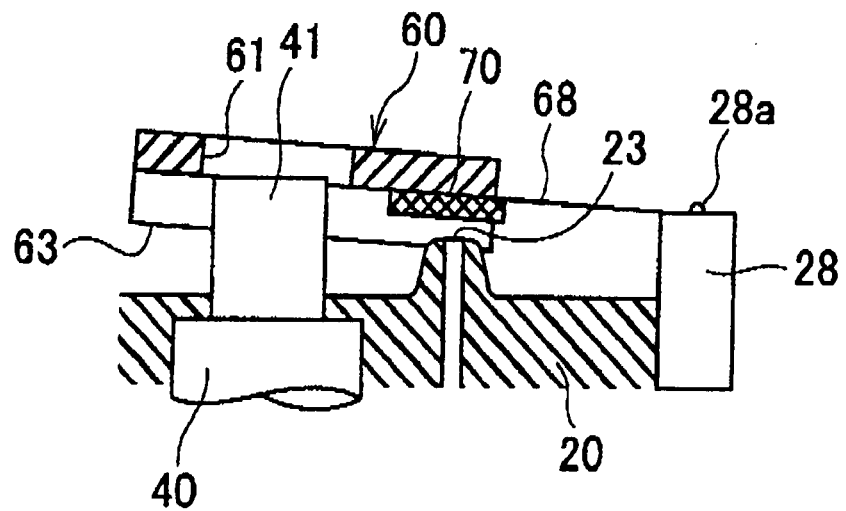
FIG. 3B is a view from the same direction as FIG. 1B.
Figure 3C:
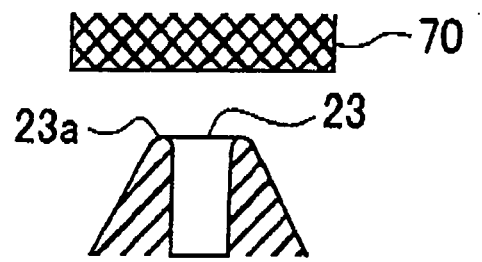
FIG. 3C shows only the relationship between the valve body and the nozzle.
Figure 4A:
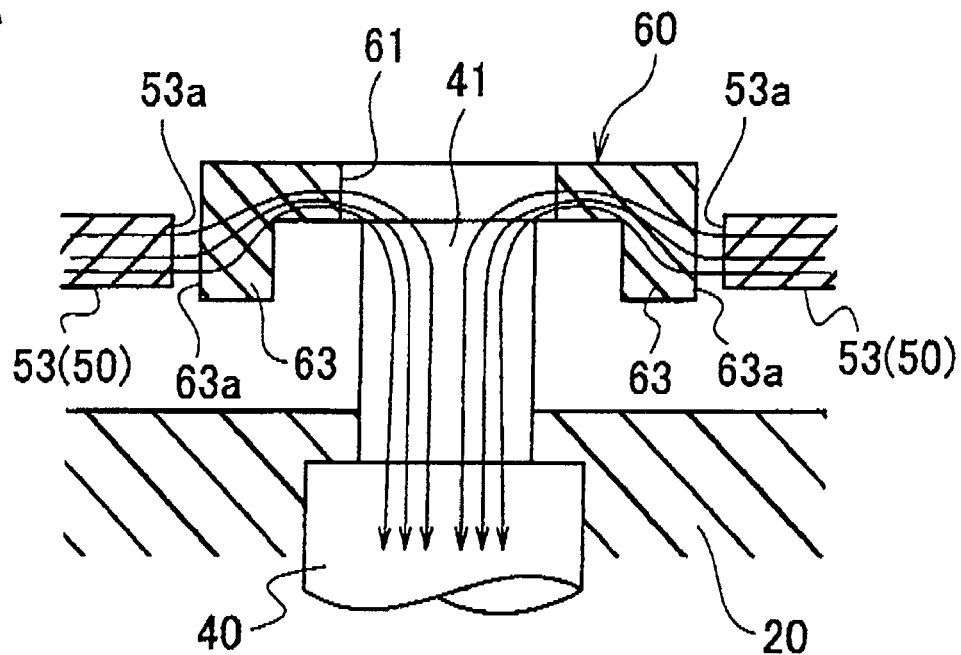
FIG. 4A is a diagram showing a simple enlargement of the relevant parts of FIG. 2B along with the path of magnetic fluxes.
Figure 4B:
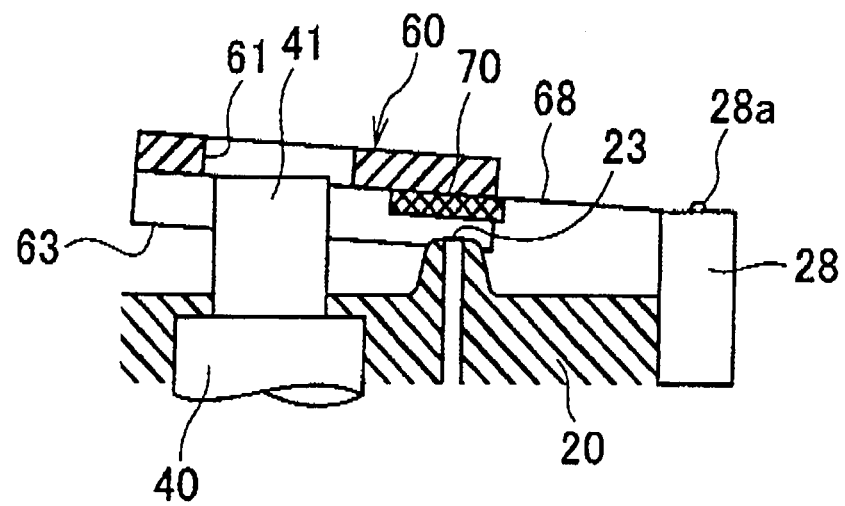
FIG. 4B is a view from the same direction as FIG. 1B.
Figure 4C:
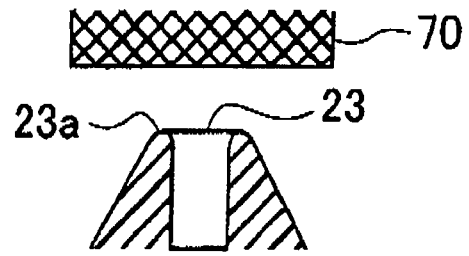
FIG. 4C shows only the relationship between the valve body and the nozzle.
Figure 5A:
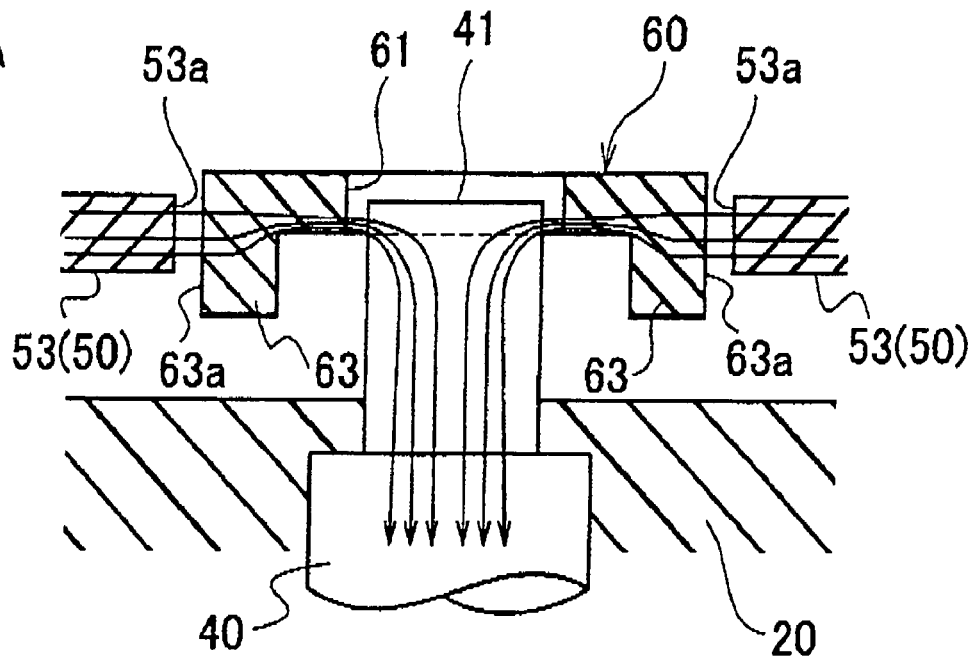
FIG. 5A is a diagram showing a simple enlargement of the relevant parts of FIG. 2C along with the path of magnetic fluxes.
Figure 5B:
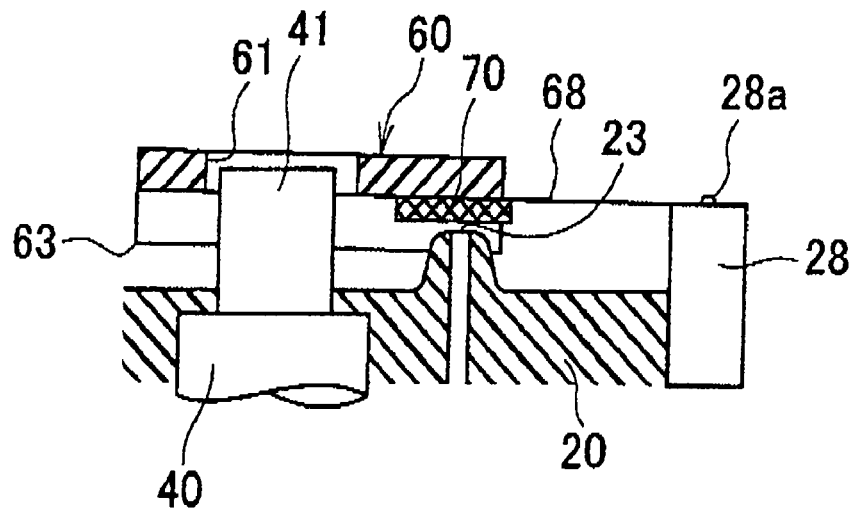
FIG. 5B is a view from the same direction as FIG. 1B.
Figure 5C:
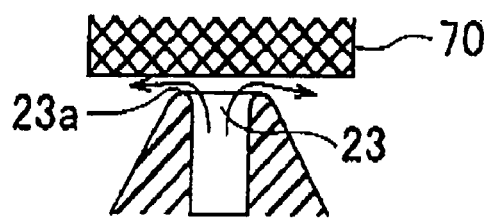
FIG. 5C shows only the relationship between the valve body and the nozzle.

FIGS. 3, 4, and 5 are schematic enlarged views showing the states of FIGS. 2A, 2B, and 2C, wherein FIGS. 3A, 4A, and 5A are diagrams showing a simple enlargement of the relevant parts of FIG. 2 along with the path of magnetic fluxes; FIGS. 3B, 4B, and 5B are views from the same direction as FIG. 1B; and FIGS. 3C, 4C, and 5C show only the relationship between the valve body and the nozzle.

As shown in FIG. 1, the electric-powered air release valve 10 is composed of a bobbin 20 that doubles as a housing, an excitation coil 30 wound onto the bobbin 20, a circular rod-shaped fixed iron core 40, a yoke 50 composed of a pressed magnetic metal sheet, a movable iron plate 60, a leaf spring 68, a terminal pin 90, and other components.

An air channel 21 that passes through the center part (region inside the coil 30) of the bobbin 20 composed of a resin molding, and a fitting hole 22 for the fixed iron core 40 are provided in the center part of the bobbin 20, and the fixed iron core 40 is inserted/fitted into the fitting hole 22 of the fixed iron core 40 from an opening at the lower end of the bobbin 20.

The fixed iron core 40 has a small-diameter circular column part 41 at one end (upper end in the drawing) in the longitudinal direction, and a distal end of the circular column 41 is inserted into the fitting hole 22 so as to protrude to the outside of the bobbin 20. Specifically, a small-diameter hole 22b is formed in one end (upper end) of the fitting hole 22 via a stepped part 22a, the circular column 41 at one end of the fixed iron core 40 is fitted into the small-diameter hole 22b, and the distal end of the circular column 41 on one end is made to protrude a certain distance to the outside of the bobbin 20 while the shoulder part is positioned against the stepped part 22a.

A nozzle 23 as an air release vent is provided to one end part of the air channel 21 formed inside the bobbin 20. The nozzle 23 is disposed in a position adjacent to the circular column 41 at one end of the fixed iron core 40, and protrudes in a chevron shape from one end surface of the bobbin 20. As shown in FIG. 3C, a rounding (R) is formed to round the peripheral edge 23a of the distal end opening of the nozzle 23 that opens at the apex of the chevron shape.

The other end part of the air channel 21 is open at the other end surface of the bobbin 20 as an air inflow vent 24, and a configuration is adopted whereby air is introduced from the air inflow vent 24 and discharged to the outside from the nozzle 23 through the air channel 21 inside the bobbin 20. The excitation coil 30 is disposed so as to surround the fixed iron core 40 and the air channel 21, and the excitation coil 30 magnetizes the fixed iron core 40 in the longitudinal direction when electrical power is applied.

The movable iron plate 60 is disposed so as to face the nozzle 23 and the circular column 41 at one end of the fixed iron core 40. When the fixed iron core 40 is magnetized, the movable iron plate 60 moves toward the nozzle 23, as shown in FIGS. 2B and 2C, from the initial position shown in FIG. 2A according to the magnetic attraction force. A rubber valve (valve body) 70 for adjusting the opening of the nozzle 23 is attached to the movable iron plate 60, and the movable iron plate 60 is attracted to the fixed iron core 40, whereby the interval (gap) between the rubber valve 70 and the nozzle 23 changes. The amount of opening of the nozzle 23 is thereby varied, and the amount of released air is varied as well.

Two circular holes 61, 62 are provided longitudinally in the center part in the transverse width direction of the movable iron plate 60 formed as a small rectangular piece. One circular hole 61 is an opening capable of accommodating the circular column 41 at one end of the fixed iron core 40 when the movable iron plate 60 is moved toward the nozzle 23, and a small magnetic gap is maintained between the internal periphery of the circular hole 61 and the external periphery of the circular column 41 at one end of the fixed iron core 40 that protrudes from the bobbin 20.

When electrical power is applied to the excitation coil 30, a magnetic attraction force is generated between the fixed iron core 40 and the movable iron plate 60 according to the drive current, the movable iron plate 60 moves toward the fixed iron core 40, and the circular column 41 at one end of the fixed iron core 40 penetrates into the circular hole 61 in the movable iron plate 60. In this case, the thickness of the movable iron plate 60 is set so as to be equal to or greater than the maximum amount of movement of the movable iron plate 60. The head part of the rubber valve 70 is fitted into and fixed in the other circular hole 62 so as to be able to press against the nozzle 23.

One end part of the leaf spring 68 for urging the movable iron plate 60 into the initial position is fitted in an end part in the longitudinal direction of the movable iron plate 60 on the side of the circular hole 62 in which the rubber valve 70 is fixed, and the other end part of the leaf spring 68 is fixed to the upper surface of a spring support part 28 of the bobbin 20. Several small protrusions 28a, 28b are provided to the spring support part 28, a small hole 68a or small notch 68b of the leaf spring 68 is fitted over the small protrusions 28a, 28b, and the small protrusions 28a, 28b are welded to the leaf spring 68, whereby the leaf spring 68 is securely fixed in position to the spring support part 28. The leaf spring 68 is fixed to the bobbin 20 in this manner, whereby the movable iron plate 60 is cantilevered by the leaf spring 68.

In this case, when viewed as a cantilever beam, the rubber valve 70 and the nozzle 23 (action point) are positioned closer to the support point of the cantilevered movable iron plate 60 (leaf spring 68) than the magnetic attraction point (power point) of the movable iron plate 60 and the fixed iron core 40. According to this principle, the rubber valve 70 can be actuated by a small drive force.

The rubber valve 70 is configured so that the amount of opening of the nozzle 23 is adjusted according to the movement position when the movable iron plate 60 is moved toward the nozzle 23 against the urging force of the leaf spring 68. The surface of the rubber valve 70 that presses against the nozzle 23 is formed as a smooth and flat surface.

The yoke 50 is formed in a U shape that has a bottom panel 51 and side panels 52, and is disposed so as to cover the outside of the excitation coil 30. The bottom panel 51 is magnetically connected to the other end part (lower end) of the fixed iron core 40. The upper ends of the side panels 52 are curved inward, and the distal end parts 53 thereof face the side parts in the transverse width direction of the movable iron plate 60 via a magnetic gap.

Curved machined parts 63 for increasing the opposing surface area are provided to the side parts of the movable iron plate 60 that face the distal end parts 53 of the yoke 50, and the external surfaces of the curved machined parts 63 and the end surfaces of the distal end parts 53 of the yoke 50 face parallel to each other. By providing the curved machined parts 63 to the movable iron plate 60 in this manner, a significant difference in the magnetic bond does not occur even when the movable iron plate 60 moves toward the fixed iron core 40 by magnetic force.

A closed-loop magnetic circuit is formed by the three components that include the fixed iron core 40, the yoke 50, and the movable iron plate 60. In this case, as shown in FIGS. 3A, 4A, and 5A, the magnetic channel in the magnetic gap between the yoke 50 and the movable iron plate 60, and the magnetic channel in the magnetic gap between the fixed iron core 40 and the movable iron plate 60, are positioned in substantially the same plane.

A groove 51a for preventing interference with the connecting part of the air inflow vent 24 is provided to the bottom panel 51 of the yoke 50. A pin support part 29 in which terminal pins 90 connected to both ends of the excitation coil 30 is provided to the upper end of the bobbin 20 on the side opposite the spring support part 28.

Figure 6:
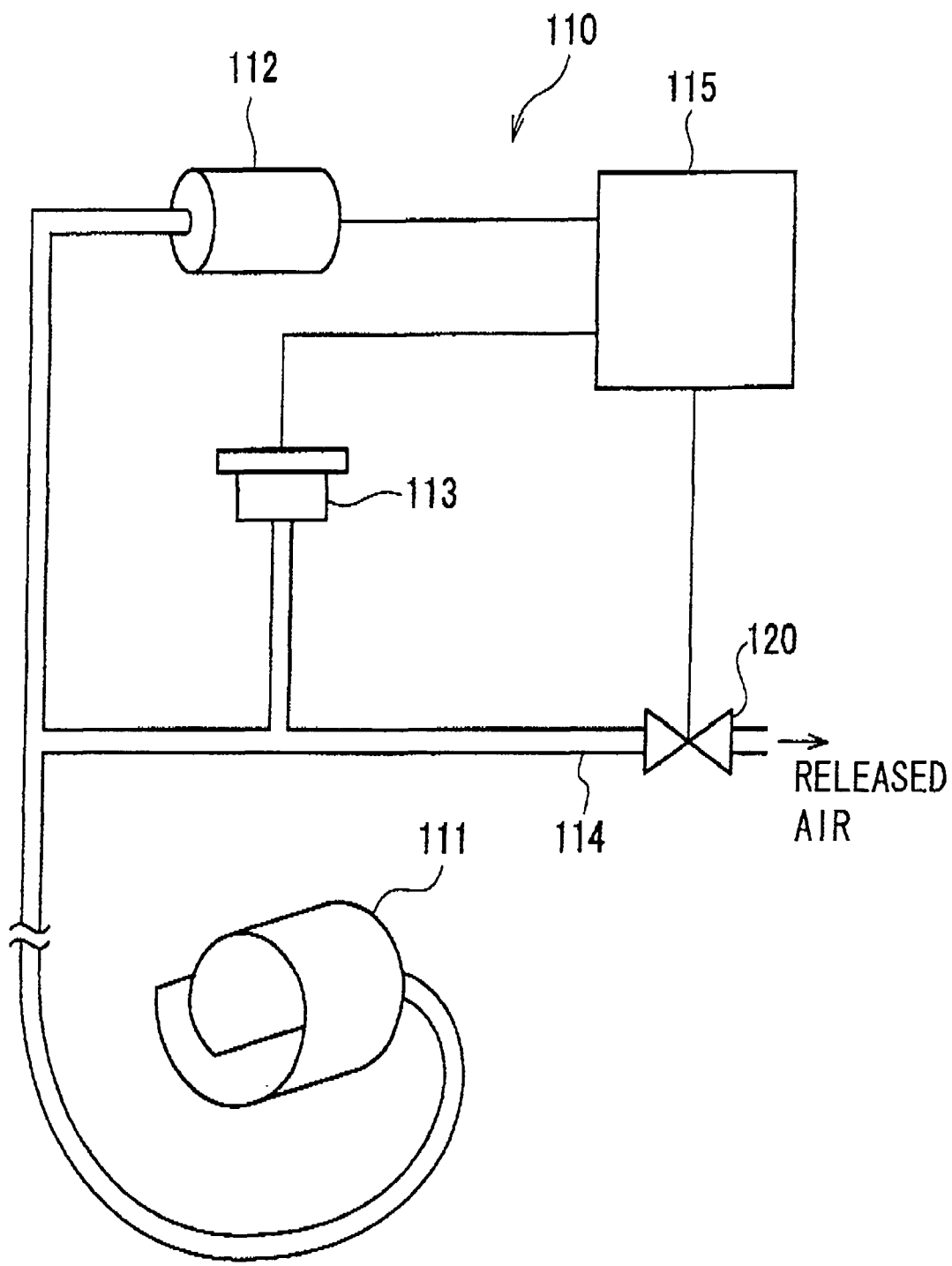
FIG. 6 is a system diagram showing an example of a blood pressure gauge equipped with the electric-powered air release valve of the present invention.
Figure 7:
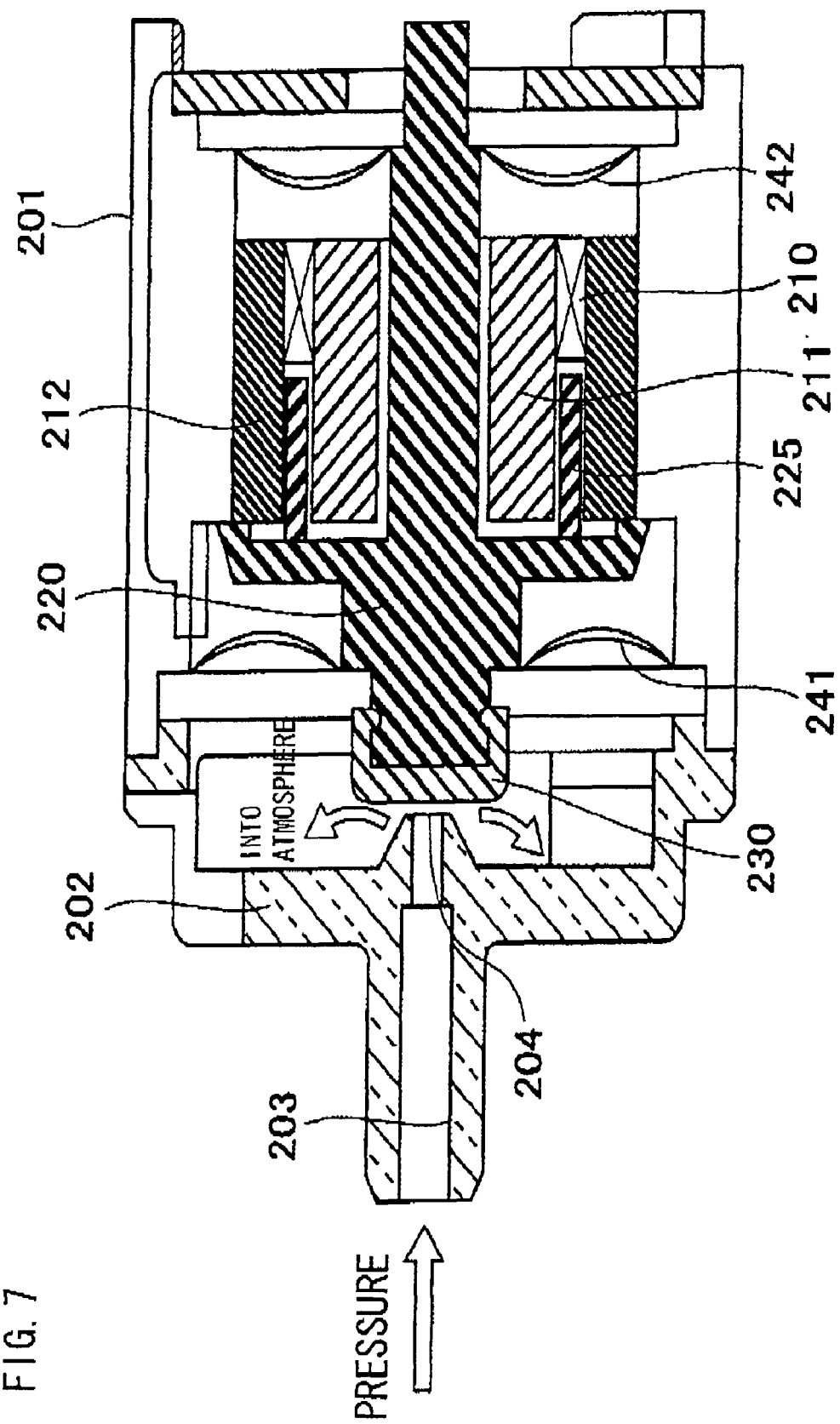
FIG. 7 is a lateral sectional view showing the conventional electric-powered air release valve.

The electric-powered air release valve 10 configured as described above cam be applied as the air release valve of a blood pressure gauge. FIG. 6 is a system diagram showing the structure of a blood pressure gauge to which the electric-powered air release valve 10 is applied.

The blood pressure gauge 110 is composed of a cuff belt 111 that is wrapped onto the arm, wrist, finger, or other part of a body; a pressurizing pump 112 for feeding compressed air to the cuff belt 111; a pressure gauge 113 for detecting the air pressure inside the cuff belt 111; an electric-powered air release valve 120 (that corresponds to the electric-powered air release valve 10) for releasing the air in the cuff belt 111 into the atmosphere at a constant rate through a conducting tube 114; and a microcomputer 115 for controlling the operation of the pressurizing pump 112 on the basis of a detection signal from the pressure gauge 113 so that air is fed at a constant pressure to the cuff belt 111, and controlling the operation of the electric-powered air release valve 120 so that air is released from the cuff belt 111 at a constant rate.

The operation of the electric-powered air release valve 10 (120) applied to the blood pressure gauge 110 as described above will next be described primarily with reference to FIGS. 2 through 5.

Before electric power is applied to the excitation coil 30, the nozzle 23 is completely unblocked by the rubber valve 70 since the movable iron plate 60 is urged to the initial position by the urging force of the leaf spring 68, as shown in FIGS. 2A and 3. At this time, the edge of the distal end of the circular column 41 at one end of the fixed iron core 40 has weak magnetic coupling with the edge of the circular hole 61 of the movable iron plate 60.

When electric power is applied to the excitation coil 30 in this state, the fixed iron core 40 is magnetized in the longitudinal direction. A magnetic attraction force then occurs between the fixed iron core 40 and the movable iron plate 60, whereby the movable iron plate 60 is attracted toward the fixed iron core 40, as shown in FIGS. 2B and 4. At this time, the external periphery of the distal end of the circular column 41 at one end of the fixed iron core 40 is slightly inside the circular hole 61 of the movable iron plate 60, and a magnetic circuit is formed in the opposing surface area.

The movable iron plate 60 is then attracted to the fixed iron core 40 to the maximum extent, and as shown in FIGS. 2C and 5, the rubber valve 70 provided to the movable iron plate 60 is pressed against the distal end of the nozzle 23 without a gap, and the nozzle 23 is completely closed. The surface area in which the fixed iron core 40 and the movable iron plate 60 oppose each other is maximized at this time, and the pressurizing pump 112 is operated in this state to feed air into the cuff belt 111 and pressurize the cuff belt 111.

The process of depressurizing the cuff belt 111 then occurs.

At this time, the magnetic force generated in the fixed iron core 40 weakens as the current fed to the excitation coil 30 is gradually reduced. The movable iron plate 60 is then moved toward the initial position by the urging force of the leaf spring 68, the rubber valve 70 separates from the nozzle 23, the gap between the nozzle 23 and the rubber valve 70 gradually opens, and the air inside the cuff belt 111 is released in minute increments through the nozzle 23, as shown in FIG. 4. Blood pressure is measured in the process of reducing the pressure inside the cuff belt 111 through this release of minute amounts of air.

The amount of movement of the rubber valve 70 when such an operation is performed is determined by a balance between the elasticity of the leaf spring 68, the air pressure in the nozzle 23, and the magnetic attraction force occurring between the fixed iron core 40 and the movable iron plate 60. The size of the gap between the rubber valve 70 and the nozzle 23 is adjusted by the position of the rubber valve 70, and the air release flow rate varies according to this adjustment.

The rubber valve 70 must be completely pressed against the distal end of the nozzle 23 in order for the nozzle 23 to be completely closed, and for air leakage to be completely stopped. The pressing force required to completely block the air is determined by the pressure exerted on the air inflow vent 24, the diameter of the opening at the distal end of the nozzle 23, the stress of the leaf spring 68, and the ratio of the distance from the support point of the leaf spring 68 to the action point (rubber valve 70) and the distance from the support point to the power point (point of attraction between the movable iron plate 60 and the fixed iron core 40).

For example, the pressing force of air from the nozzle 23 is first obtained from the following calculation, wherein the maximum pressure of the operating range of the blood pressure gauge is 300 mmHg ($=407$ g/cm$^2$), the diameter of the distal end opening of the nozzle 23 is 0.5 mm, and the ratio of the distance from the support point to the action point and the distance from the support point to the power point is ½.

$$\text{Pressing force of air from nozzle} = pr^2 \times 407/100$$
$$= 3.14 \times (0.5/2)^2 \times 407/100$$
$$= 0.779 \text{ g}$$

Since the elastic stress of the leaf spring 68 is added to the above result, the force on the movable iron plate 60 required to completely block the air is obtained from the following calculation in which the elastic stress of the leaf spring 68 is assumed to be 2 g.

$$\frac{\text{Force exerted on movable iron}}{\text{plate to completely block the air}} = (2 + 0.799)/2$$
$$= 1.3995 \text{ g}$$

Accordingly, the nozzle 23 is completely closed when the movable iron plate 60 is attracted to the fixed iron core 40 with a force of approximately 1.4 g or greater. When the force is less than this amount, the leaf spring 68 bends to the position at which there is a balance between the sum of the air pressing force and the stress of the leaf spring 68, and the drive force on the movable iron plate exerted by the magnetic force. The gap between the rubber valve 70 and the nozzle 23 is determined, and the amount of air leakage is adjusted according to the amount of movement.

In the electric-powered air release valve 10 of the present embodiment, the fixed iron core 40 is magnetized by the application of electric power to the excitation coil 30, and the movable iron plate 60 is attracted by the magnetic force, whereby the amount of opening of the nozzle 23 is adjusted by the rubber valve 70 provided to the movable iron plate 60. A small-sized, compact, and low-cost structure that is simple and has a small number of parts can therefore be created without the use of a permanent magnet having a high unit cost.

Instead of a movable coil system, a system is adopted in which the movable iron plate 60 equipped with the rubber valve 70 is attracted by the magnetic force generated in the fixed iron core 40 to adjust the valve opening. Therefore, unlike the conventional movable coil system, the weight of the moving parts can be reduced, and a simpler assembly process that includes attachment of the leaf spring 68 can be anticipated.

Since it is possible to reduce the weight of the moving parts that play an important role in adjusting the opening of the nozzle, it is possible to minimize variations in the valve characteristics caused by the weight of the device acting in different directions according to differences in posture. For example, in applications such as wrist-type blood-pressure gauges that are highly likely to be used in a variety of postures, stable characteristics can be demonstrated, and highly precise measurement can be performed.

A magnetic circuit is formed by the fixed iron core 40, the yoke 50, and the movable iron plate 60 that are each provided via a magnetic gap. Leakage of magnetic fluxes is therefore reduced, and current control can be performed with high efficiency and minimal drive loss.

In general, as the current flowing through the excitation coil 30 is increased, the movable iron plate 60 continues to be attracted to the fixed iron core 40 according to the generated electromagnetic force. The attractive force then increases in inverse proportion to the square of the distance between the movable iron plate 60 and the fixed iron core 40. In this regard, the electric-powered air release valve 10 of the present embodiment is configured so that a circular hole 61 is formed in the movable iron plate 60, the circular column 41 at one end of the fixed iron core 40 penetrates into the circular hole 61 according to the movement of the movable iron plate 60, and a magnetic gap is maintained between the internal periphery of the circular hole 61 and the external periphery of the circular column 41 at one end of the fixed iron core 40.

Therefore, even when the movable iron plate 60 moves according to the magnetic force, the size of the magnetic gap between the movable iron plate 60 and the fixed iron core 40 can be kept substantially constant.

The force of magnetic attraction increases in inverse proportion to the square of the distance (size of the magnetic gap), as previously mentioned. However, since the magnetic gap can be kept substantially constant in the electric-powered air release valve 10 of the present embodiment, the relationship between the current fed to the excitation coil 30 and the amount of movement of the movable iron plate 60 can be made approximately linear, and there is no abrupt attraction of the movable iron plate 60 to the fixed iron core 40 as the amount of movement is increased (as the distance decreases in size). In other words, the size of the gap between the nozzle 23 and the rubber valve 70 can be controlled in approximate proportion to the amount of supplied current, and this gap control enables the amount of released air to be controlled with high precision.

As a result, when the present invention is applied as the air release valve of a blood pressure gauge, the control characteristics at extremely low pressure reduction rates can be improved, and blood pressure can be measured with high precision and with stable pressure reduction characteristics.

In a structure in which the movable iron plate 60 is merely attached by suction parallel to the attachment surface of the fixed iron core 40, the force of the attachment increases in inverse proportion to the square of the distance. Therefore, when an attempt is made to control the gap with the nozzle 23 using the rubber valve 70 to which the movable iron plate 60 is attached, the gap becomes difficult to control as the gap is reduced. Accordingly, it is difficult to increase the precision with which minute amounts of airflow are controlled through management of the gap.

Therefore, to address this problem, irregularities are provided to the surface of the rubber valve 70 that presses against the nozzle 23, the minute gap is substantially managed by the degree to which the irregularities of the rubber valve 70 are collapsed when the rubber valve 70 is pressed against the nozzle 23, and the amount of air released from the gap (amount of leakage) is adjusted in the conventional technique described in Japanese Laid-open Patent Application No. 2005-155898. However, since the collapsibility characteristics the rubber valve 70 are dependent on the hardness of the rubber, and the hardness of the rubber can vary significantly between product lots, the degree to which the rubber valve 70 can be collapsed is difficult to manage on the basis of a constant assumed rubber hardness. Designed air release characteristics are therefore difficult to obtain when this approach is taken in a mass production system.

In this regard, the electric-powered air release valve 10 of the present embodiment does not employ a system that depends on the degree to which the rubber valve 70 can be collapsed to perform subtle adjustments of the flow rate, but instead controls the air release flow rate by carefully managing the space (gap) between the rubber valve 70 and the nozzle 23 with high precision, as previously described. Accordingly, there is no need for dependence on the hardness of the rubber, and the rubber is therefore easy to select. Since there is also no need to manage the essential minute gap according to the degree in which the surface irregularities of the rubber valve 70 can be collapsed, the surface of the rubber valve 70 may simply be a flat surface that has a level of smoothness that prevents adhesion to the nozzle 23. As a result, the air releasing characteristics of each product in the mass production system are easier to manage, and design/manufacture is facilitated.

In the electric-powered air release valve 10 of the present embodiment, the movable iron plate 60 is composed of a sheet material whose thickness is equal to or greater than the maximum amount of movement of the movable iron plate 60. Therefore, opposing surface area of the movable iron plate 60 and the fixed iron core 40 varies to a certain degree with changes in the degree to which the circular column 41 at one end of the fixed iron core 40 penetrates into the circular hole 61 within the range of the thickness of the movable iron plate 60, and almost no change is produced in the size of the magnetic gap. Accordingly, the linearity of control can easily be maintained merely by considering the thickness of the sheet material when selecting the material for forming the movable iron plate 60. Since the movable iron plate 60 is also formed from a sheet material, the circular hole 61 can easily by formed by punching.

In the electric-powered air release valve 10 of the present embodiment, a circular hole 61 is formed in the center part in the width direction of the movable iron plate 60, and a circular column 41 that can be accommodated by the circular hole 61 is formed at one end part of the fixed iron core 40, A relationship can therefore be established in which the peripheral surfaces face each other via the magnetic gap. Accordingly, effects are obtained whereby bias in the distribution of magnetic fluxes can be minimized, and stable attraction effects can be exerted. Since the circular hole 61 of the movable iron plate 60, as well as the circular column 41 at one end of the fixed iron core 40, have shapes that are relatively easy to machine compared to other shapes, dimensional precision is easily obtained, and the distance between the movable iron plate 60 and the opposing part of the fixed iron core 40, i.e., the magnetic gap, can be reduced. As a result, narrowing the magnetic gap also has the effect of making it easier to increase the drive force.

The relationship between the circular hole 61 and the circular column 41 is also advantageous for assembly. For example, during assembly, a tubular positioning tool is inserted in the gap between the circular column 41 of the fixed iron core 40 and the circular hole 61 of the movable iron plate 60, and the fixed iron core 40 and movable iron plate 60 are assembled thereon. Both components can thereby be easily positioned, and the precision of assembly can also be increased.

In the electric-powered air release valve 10 of the present embodiment, the distal end parts 53 of the yoke 50 are disposed so as to face the side parts of the movable iron plate 60 via the magnetic gap, and curved machined parts 63 for increasing the opposing surface area are provided to the side parts of the movable iron plate 60 that face the end surfaces of the distal end parts 53 of the yoke 50. The surface area of the magnetic bond can thereby be increased, and the efficiency of the magnetic circuit can be improved.

Furthermore, a magnetic channel between the movable iron plate 60 and the yoke 50, and a magnetic channel between the movable iron plate 60 and the fixed iron core 40 are disposed in substantially the same plane. Therefore, the path of magnetism from the yoke 50 to the fixed iron core 40 through the movable iron plate 60 can be in a straight line of minimum length, magnetic circuit loss can be reduced, and enhanced drive efficiency can be anticipated.

In the electric-powered air release valve 10 of the present embodiment, the fixed iron core 40 and the air channel 21 are each provided to the inside of the bobbin 20 onto which the excitation coil 30 is wound. Therefore, the nozzle 23 and the rubber valve 70 can be disposed in a position that is near the point of magnetic attraction between the movable iron plate 60 and the fixed iron core 40, and the structure that also includes the support part of the movable iron plate 60 can be reduced in size and made simple and compact.

The fitting hole 22 and air channel 21 of the fixed iron core 40 are also integrally formed inside a bobbin 20 made of resin, and the nozzle 23 is integrally formed in an end surface of the bobbin 20. The structure can therefore be simplified, and easy assembly and enhanced production properties can be anticipated.

In the electric-powered air release valve 10 of the present embodiment, the movable iron plate 60 is cantilevered by the bobbin 20 via a leaf spring 68, and the nozzle 23 and rubber valve 70 (action point) are disposed between the movable iron plate 60 and a magnetic attraction point (power point) of the fixed iron core 40 at a point (support point) at which the movable iron plate 60 is supported. Therefore, the magnetic attraction force acting between the movable iron plate 60 and the fixed iron core 40 can be effectively transmitted as the force for adjusting the gap between the nozzle 23 and the rubber valve 70. In other words, the rubber valve 70 can be moved by a small drive force, and enhanced drive efficiency is anticipated. The placement of the action point (valve body) between the support point (cantilever point) and the power point (magnetic attraction point) helps to reduce the size of the area around the moving part.

It is also possible to place the nozzle 23 and the rubber valve 70 outside the excitation coil 30 wound onto the bobbin. In this case, however, the distance between the support point and the power point, and the distance between the action point and the power point must be increased, which inhibits size reduction. In this regard, a placement such as the one used in the present electric-powered air release valve 10 contributes to reduced size. Since the movable iron plate 60 may also be supported via a cantilevered leaf spring 68, the movable iron plate 60 can be installed by a simple process, A leaf spring 68 is also used as the device for urging the movable iron plate 60, Therefore, the movable iron plate 60 can easily be supported while receiving the urging force, and this arrangement is also effective for making the structure more compact.

In the electric-powered air release valve 10 of the present embodiment, the distal end of the nozzle 23 protrudes in a chevron shape, the peripheral edge 23a of the distal-end opening of the nozzle 23 is rounded, and the surface of the rubber valve 70 that presses against the nozzle 23 is formed as a smooth flat surface. The nozzle 23 and the rubber valve 70 can therefore be brought into contact with each other in a form that approximates line contact rather than plane contact, The gap between the nozzle 23 and the rubber valve 70 thus becomes easier to manage, and the air release flow rate can be made easier to control. Since the surface of the rubber valve 70 that presses against the nozzle 23 can be made smooth and flat, machining is facilitated and production capability can be enhanced.

Since the rubber valve 70 is also used as the valve body, the completely closed nozzle can be made more airtight. As previously described, flow rate adjustment is performed by carefully managing the gap between the rubber valve 70 and the nozzle 23, and not according to the degree to which the rubber can be collapsed. Therefore, the hardness of the rubber valve 70 can be freely selected, and design/manufacturing is facilitated.

In the embodiment described above, the surface area opposing the distal end parts 53 of the yoke 50 was increased by providing curved machined parts 63 to the side parts of the movable iron plate 60, but the same effects can be obtained when curved machined parts are provided on the side of the distal end parts 53 of the yoke 50. The curved machined parts may also be provided to both the side parts of the movable iron plate 60 and the distal end parts 53 of the yoke 50.

A case was described in the embodiment above in which a circular hole 61 was provided to the movable iron plate 60, and a circular column 41 capable of being accommodated in the circular hole 61 was provided to one end part of the fixed iron core 40, but the shape of the opening in the movable iron plate 60 is not limited to a circular hole 61, and may be any shape. However, the shape of the opening in the movable iron plate 60 must at least correspond to the shape of the end part of the fixed iron core 40 in order to obtain a uniform magnetic gap.

A case was described in the embodiment above in which the fitting hole 22 and the air channel 21 of the fixed iron core 40 were formed directly in the bobbin 20, but a configuration may also be adopted in which the bobbin 20 is formed so as to be hollow, and the fixed iron core 40 and the air channel 21 are merely provided in the space inside the bobbin 20.

What is claimed is:

1. An electric-powered air release valve comprising:
   a nozzle provided as an air discharge vent to an end part of an air channel;
   a rod-shaped fixed iron core disposed so that an end part in a longitudinal direction is aligned with the nozzle on the same side as the nozzle;
   an excitation coil provided so as to surround the fixed iron core, for magnetizing the fixed iron core in a longitudinal direction when electrical power is applied;
   a movable iron plate that is disposed so as to face said nozzle and an end part of said fixed iron core and that moves toward said nozzle from an initial position according to a magnetic attraction force when said fixed iron core is magnetized
   a spring for urging the movable iron plate into said initial position;
   a valve body provided to said movable iron plate, for adjusting an opening amount of said nozzle in accordance with a movement position when the movable iron plate moves toward said nozzle in opposition to an urging force of said spring; and
   a yoke that is magnetically connected to another end part of said fixed iron core, and whose distal end part is disposed opposite a position separated from an end part of said fixed iron core above said movable iron plate, via a magnetic gap;
   wherein an opening is formed in said movable iron plate that is capable of accommodating an end part of said fixed iron core when the movable iron plate is moved toward said nozzle, and a magnetic gap is maintained between an internal periphery of the opening and an external periphery of an end part of said fixed iron core;
   said fixed iron core and said air channel are each provided to an internal side or interior of a bobbin onto which said excitation coil is wound; and
   said bobbin is composed of a resin molding having said air channel and a fitting hole for said fixed iron core; said fixed iron core is fitted into said fitting hole so that one end part of said fitted iron core protrudes from an end of said fitting hole, and a nozzle of one end part of said air channel is provided in a position adjacent to one end part of the fixed iron core so as to protrude from one end surface of said bobbin; and another end part of said air channel is provided as an inflow vent to another end surface of said bobbin.

2. The electric-powered air release valve according to claim 1, wherein said movable iron plate is composed of a panel having a thickness equal to or greater than a maximum amount of movement of the movable iron plate.

3. The electric-powered air release valve according to claim 2, wherein
a circular hole is formed as said opening in a center part of a width direction of said movable iron plate; and
a circular column that can be accommodated by said circular hole is formed at an end part of said fixed iron core.

4. The electric-powered air release valve according to claim 2, wherein
a distal end part of said yoke is disposed so as to face side parts of said movable iron plate via said magnetic gap; and
a curved machined part for increasing an opposing surface area is provided to at least one area selected from the distal end of said yoke and side parts of the movable iron plate, disposed so as to face each other.

5. The electric-powered air release valve according to claim 2, wherein a magnetic channel through said movable iron plate and said magnetic gap of the yoke, and a magnetic channel through said movable iron plate and said magnetic gap of the fixed iron core, are disposed in substantially the same plane.

6. The electric-powered air release valve according to claim 2, wherein
a distal end of said nozzle protrudes in a chevron shape;
a peripheral edge of a distal-end opening of the nozzle is rounded; and
a surface of said valve body that presses against the nozzle is formed as a smooth flat surface.

7. The electric-powered air release valve according to claim 2, wherein a rubber valve for pressing against a distal end of said nozzle is provided as said valve body.

8. The electric-powered air release valve according to claim 1, wherein
a circular hole is formed as said opening in a center part of a width direction of said movable iron plate; and
a circular column that can be accommodated by said circular hole is formed at an end part of said fixed iron core.

9. The electric-powered air release valve according to claim 8, wherein
a distal end part of said yoke is disposed so as to face side parts of said movable iron plate via said magnetic gap; and
a curved machined part for increasing an opposing surface area is provided to at least one area selected from the distal end of said yoke and side parts of the movable iron plate, disposed so as to face each other.

10. The electric-powered air release valve according to claim 1, wherein
a distal end part of said yoke is disposed so as to face side parts of said movable iron plate via said magnetic gap; and
a curved machined part for increasing an opposing surface area is provided to at least one area selected from the distal end of said yoke and side parts of the movable iron plate, disposed so as to face each other.

11. The electric-powered air release valve according to claim 1, wherein
a magnetic channel through said movable iron plate and said magnetic gap of the yoke, and
a magnetic channel through said movable iron plate and said magnetic gap of the fixed iron core, are disposed in substantially the same plane.

12. The electric-powered air release valve according to claim 1, wherein
a distal end of said nozzle protrudes in a chevron shape;
a peripheral edge of a distal-end opening of the nozzle is rounded; and
a surface of said valve body that presses against the nozzle is formed as a smooth flat surface.

13. The electric-powered air release valve according to claim 1, wherein a rubber valve for pressing against a distal end of said nozzle is provided as said valve body.

14. An electric-powered air release valve comprising:
a nozzle provided as an air discharge vent to an end part of an air channel;
a rod-shaped fixed iron core disposed so that an end part in a longitudinal direction is aligned with the nozzle on the same side as the nozzle;
an excitation coil provided so as to surround the fixed iron core, for magnetizing the fixed iron core in a longitudinal direction when electrical power is applied;
a movable iron plate that is disposed so as to face said nozzle and an end part of said fixed iron core and that moves toward said nozzle from an initial position according to a magnetic attraction force when said fixed iron core is magnetized;
a spring for urging the movable iron plate into said initial position;
a valve body provided to said movable iron plate, for adjusting an opening amount of said nozzle in accordance with a movement position when the movable iron plate moves toward said nozzle in opposition to an urging force of said spring; and,
a yoke that is magnetically connected to another end part of said fixed iron core, and whose distal end part is disposed opposite a position separated from an end part of said fixed iron core above said movable iron plate, via a magnetic gap;
wherein an opening is formed in said movable iron plate that is capable of accommodating an end part of said fixed iron core when the movable iron plate is moved toward said nozzle, and a magnetic gap is maintained between an internal periphery of the opening and an external periphery of an end part of said fixed iron core;
said fixed iron core and said air channel are each provided to an internal side or interior of a bobbin onto which said excitation coil is wound; and,
said movable iron plate is cantilevered by said bobbin via a leaf spring as said spring; and said nozzle and valve body are disposed between said movable iron plate and a magnetic attraction point of the fixed iron core at a point at which said movable iron plate is supported.

15. The electric-powered air release valve according to claim 14, wherein said movable iron plate is composed of a panel having a thickness equal to or greater than a maximum amount of movement of the movable iron plate.

16. The electric-powered air release valve according to claim 14, wherein
a circular hole is formed as said opening in a center part of a width direction of said movable iron plate; and
a circular column that can be accommodated by said circular hole is formed at an end part of said fixed iron core.

17. The electric-powered air release valve according to claim 14, wherein
a distal end part of said yoke is disposed so as to face side parts of said movable iron plate via said magnetic gap; and
a curved machined part for increasing an opposing surface area is provided to at least one area selected from the distal end of said yoke and side parts of the movable iron plate, disposed so as to face each other.

18. The electric-powered air release valve according to claim 14, wherein
a magnetic channel through said movable iron plate and said magnetic gap of the yoke, and
a magnetic channel through said movable iron plate and said magnetic gap of the fixed iron core, are disposed in substantially the same plane.

19. The electric-powered air release valve according to claim 14, wherein
a distal end of said nozzle protrudes in a chevron shape;
a peripheral edge of a distal-end opening of the nozzle is rounded; and
a surface of said valve body that presses against the nozzle is formed as a smooth flat surface.

20. The electric-powered air release valve according to claim 14, wherein
a rubber valve for pressing against a distal end of said nozzle is provided as said valve body.

21. A blood gauge comprising:
a cuff belt for wrapping onto an arm, wrist, or other part of a body;
a pressurizing pump for feeding compressed air to the cuff belt;
a pressure gauge for detecting the air pressure inside the cuff belt;
an electric-powered air release valve for releasing the air in the cuff belt at a constant rate; and
a microcomputer for controlling the operation of the pressurizing pump on the basis of a detection signal from the pressure gauge so that air is fed at a constant pressure to the cuff belt, and controlling the operation of the electric-powered air release valve so that air is released from the cuff belt at a constant rate,
wherein the electric-powered air release valve comprises:
a nozzle provided as an air discharge vent to an end part of an air channel;
a rod-shaped fixed iron core disposed so that an end part in a longitudinal direction is aligned with the nozzle on the same side as the nozzle;
an excitation coil provided so as to surround the fixed iron core, for magnetizing the fixed iron core in a longitudinal direction when electrical power is applied;
a movable iron plate that is disposed so as to face said nozzle and an end part of said fixed iron core and that moves toward said nozzle from an initial position according to a magnetic attraction force when said fixed iron core is magnetized;
a spring for urging the movable iron plate into said initial position;
a valve body provided to said movable iron plate, for adjusting an opening amount of said nozzle in accordance with a movement position when the movable iron plate moves toward said nozzle in opposition to an urging force of said spring; and
a yoke that is magnetically connected to another end part of said fixed iron core, and whose distal end part is disposed opposite a position separated from an end part of said fixed iron core above said movable iron plate, via a magnetic gap;
wherein an opening is formed in said movable iron plate that is capable of accommodating an end part of said fixed iron core when the movable iron plate is moved toward said nozzle, and a magnetic gap is maintained between an internal periphery of the opening and an external periphery of an end part of said fixed iron core;
said fixed iron core and said air channel are each provided to an internal side or interior of a bobbin onto which said excitation coil is wound; and
said bobbin is composed of a resin molding having said air channel and a fitting hole for said fixed iron core; said fixed iron core is fitted into said fitting hole so that one end part of said fitted iron core protrudes from an end of said fitting hole, and a nozzle of one end part of said air channel is provided in a position adjacent to one end part of the fixed iron core so as to protrude from one end surface of said bobbin; and another end part of said air channel is provided as an inflow vent to another end surface of said bobbin.

22. The blood gauge according to claim 21, wherein said movable iron plate is composed of a panel having a thickness equal to or greater than a maximum amount of movement of the movable iron plate.

23. A blood gauge comprising:
a cuff belt for wrapping onto an arm, wrist, or other part of a body;
a pressurizing pump for feeding compressed air to the cuff belt;
a pressure gauge for detecting the air pressure inside the cuff belt;
an electric-powered air release valve for releasing the air in the cuff belt at a constant rate; and,
a microcomputer for controlling the operation of the pressurizing pump on the basis of a detection signal from the pressure gauge so that air is fed at a constant pressure to the cuff belt, and controlling the operation of the electric-powered air release valve so that air is released from the cuff belt at a constant rate,
wherein the electric-powered air release valve comprises:
a nozzle provided as an air discharge vent to an end part of an air channel;
a rod-shaped fixed iron core disposed so that an end part in a longitudinal direction is aligned with the nozzle on the same side as the nozzle;
an excitation coil provided so as to surround the fixed iron core, for magnetizing the fixed iron core in a longitudinal direction when electrical power is applied;
a movable iron plate that is disposed so as to face said nozzle and an end part of said fixed iron core and that moves toward said nozzle from an initial position according to a magnetic attraction force when said fixed iron core is magnetized;
a spring for urging the movable iron plate into said initial position;
a valve body provided to said movable iron plate, for adjusting an opening amount of said nozzle in accordance with a movement position when the movable iron plate moves toward said nozzle in opposition to an urging force of said spring; and
a yoke that is magnetically connected to another end part of said fixed iron core, and whose distal end part is disposed opposite a position separated from an end part of said fixed iron core above said movable iron plate, via a magnetic gap;
wherein an opening is formed in said movable iron plate that is capable of accommodating an end part of said fixed iron core when the movable iron plate is moved toward said nozzle, and a magnetic gap is maintained between an internal periphery of the opening and an external periphery of an end part of said fixed iron core;
said fixed iron core and said air channel are each provided to an internal side or interior of a bobbin onto which said excitation coil is wound; and said movable iron plate is cantilevered by said bobbin via a leaf spring as said spring; and said nozzle and valve body are disposed between said movable iron plate and a magnetic attraction point of the fixed iron core at a point at which said movable iron plate is supported.

24. The blood gauge according to claim 23, wherein said movable iron plate is composed of a panel having a thickness equal to or greater than a maximum amount of movement of the movable iron plate.

* * * * *